US005955351A

United States Patent [19]

Gerdes et al.

[11] Patent Number: 5,955,351

[45] Date of Patent: Sep. 21, 1999

[54] SELF-CONTAINED DEVICE INTEGRATING NUCLEIC ACID EXTRACTION AMPLIFICATION AND DETECTION

[76] Inventors: John C. Gerdes, 375 Steele St., Denver, Colo. 80206; Lynn D. Jankovsky, 19 Belleview La., Greenwood Village, Colo. 80121; Diane L. Kozwich, 4915 S. Huron St., Englewood, Colo. 80110

[21] Appl. No.: 08/679,522

[22] Filed: Jul. 12, 1996

Related U.S. Application Data

[60] Provisional application No. 60/000,885, Jul. 13, 1995.

[51] Int. Cl.[6] .......... C12M 1/00; G01N 15/06; G05D 16/00; C12N 15/00

[52] U.S. Cl. .......... 435/287.2; 422/68.1; 422/112; 436/810; 935/76; 935/77; 935/78; 435/6; 435/91.2

[58] Field of Search .......... 435/287.2, 6, 91.2; 422/68.1, 112; 436/810; 935/76, 77, 78

[56] References Cited

U.S. PATENT DOCUMENTS

| | | | |
|---|---|---|---|
| 4,458,020 | 7/1984 | Bohn et al. . | |
| 4,683,195 | 7/1987 | Mullis et al. . | |
| 4,683,202 | 7/1987 | Mullis et al. . | |
| 4,687,732 | 8/1987 | Ward et al. . | |
| 4,965,188 | 10/1990 | Mullis et al. . | |
| 5,116,576 | 5/1992 | Stanley . | |
| 5,130,238 | 7/1992 | Malek et al. . | |
| 5,141,850 | 8/1992 | Cole et al. . | |
| 5,230,864 | 7/1993 | Columbus . | |
| 5,244,635 | 9/1993 | Rabson et al. . | |
| 5,310,650 | 5/1994 | McMahon et al. . | |
| 5,328,825 | 7/1994 | Warren, III et al. . | |
| 5,344,757 | 9/1994 | Holtke et al. . | |
| 5,374,524 | 12/1994 | Miller . | |
| 5,387,510 | 2/1995 | Wu . | |
| 5,415,839 | 5/1995 | Zaun et al. . | |
| 5,455,166 | 10/1995 | Walker . | |
| 5,527,673 | 6/1996 | Reinhartz et al. . | |
| 5,639,428 | 6/1997 | Cottingham | 422/112 |

FOREIGN PATENT DOCUMENTS

| | | |
|---|---|---|
| 063879 | of 0000 | European Pat. Off. . |
| 173251 | of 0000 | European Pat. Off. . |
| 320308 | of 0000 | European Pat. Off. . |
| 95/01359 | of 0000 | WIPO . |

OTHER PUBLICATIONS

Sambrook, J. et al. (1989) Molecular Cloning: A Laboratory Manual, 2nd Ed., pp. 13.70–13.72, Cold Spring Harbor Laboratory, Cold Spring Harbor, N.Y.

Watson, J.D., et al. (1987) Molecular Biology of the Gene, 4th Ed., pp. 299–301, Benjamin/Cummings Pub., Menlo Park, CA.

Walker et al. (1992) PNAS 89:392.

*Primary Examiner*—W. Gary Jones
*Assistant Examiner*—Ethan Whisenant
*Attorney, Agent, or Firm*—Julie L. Bernard

[57] ABSTRACT

A self-contained device is described that integrates nucleic acid extraction, specific target amplification and detection into a single device. This integration permits rapid and accurate nucleic acid sequence detection. The invention may be used, for example, in the screening for nucleic acid sequences which may be indicative of genetic defects or contagious diseases, as well as for monitoring efficacy in the treatment of contagious diseases.

9 Claims, 11 Drawing Sheets

SELF-CONTAINED DEVICE INTEGRATING NUCLEIC ACID EXTRACTION AMPLIFICATION AND DETECTION

RELATED APPLICATIONS

This application claims priority to provisional patent application Ser. No. 06/000,885, filed Jul. 13, 1995.

FIELD OF INVENTION

This invention relates to the general fields of molecular biology and medical science, and specifically to a method of extracting nucleic acid, amplifying specific target sequences, and detecting amplified nucleic acid sequences in a self-contained device. This application, thus, describes a self-contained device capable of rapid and accurate detection of target nucleic acid sequences.

BACKGROUND AND PRIOR ART

The use of nucleic acid probe tests based on hybridization in routine clinical laboratory procedures is hindered by lack of sensitivity. The ability to amplify nucleic acids from clinical samples has greatly advanced nucleic acid probe technology, providing the sensitivity lacking in earlier versions of non-isotopic assays. Sensitivity afforded by oligonucleotide probe tests utilizing nucleic acid amplification now exceeds that of any other method. Nucleic acid amplification procedures can detect a single copy of a specific nucleic acid sequence. Routine detection and identification of specific gene sequences have extremely broad application in a number of settings and industries.

The major barrier for the transfer of technology to routine field testing is the absence of an economical and easy-to-use system or apparatus. In order to compete in today's cost conscious environment, genetic based testing must provide for high throughput, while incorporating adequate controls and safeguards to prevent false positive results due to sample cross-contamination.

Current technology involves several steps, although recent developments are directed toward automating systems for detection of the amplified target sequence. The first step, extraction of nucleic acids, is accomplished in a variety of ways, for example, phenol extraction, chaotropic reagent extraction, chromatographic purification (Qiagen, WO 95/01359, purification on silica membranes, specifically incorporated herein) and ultracentrifugation (Sambrook et al. (1989) *Molecular Cloning: A Laboratory Manual,* 2nd Ed., Cold Spring Harbor Laboratory, Cold Spring Harbor, N.Y.), specifically incorporated herein). Phenol is a well-established health hazard and requires special handling for waste removal. The extraction method is also tedious and labor intensive. Ultracentrifugation often requires the use of expensive and hazardous chemicals as well as the use of sophisticated and costly equipment. The process often requires long run times, sometimes involving one or more days of centrifugation. The easiest and fastest method is separation using chromatography purification.

The second step, the amplification of the target nucleic acid, employs a variety of enzymes known as polymerases and ligases. Polymerase chain reaction (PCR) is the most commonly used amplification technique. The general principles and conditions for amplification of nucleic acids using PCR are quite well known in the art; the details of which are provided in numerous references including U.S. Pat. No. 4,683,195, U.S. Pat. No. 4,683,202 and U.S. Pat. No. 4,965,188, all to Mullis et al., all of which are specifically incorporated herein. Thus, the details of PCR technology are not included herein. Other approaches include ligase chain reaction, Qβ replicase, strand displacement assay, transcription mediated iso CR cycling probe technology and nucleic acid sequence-based amplification (NASBA).

A current protein detection technology for antigen-antibody assays involves the use of microparticles. Furthermore, a variety of microparticle strategies for dipstick detection antigen-antibody assays are currently available, for example, a currently marketed at-home pregnancy test (U.S. Pat. No. 5,141,850 to Cole et al., specifically incorporated herein). Such tests use dyed particles that form a visible line following a specific antigen-antibody reaction. The instant invention is accomplished by hybridization of amplicons to capture oligonucleotides bound to microparticles. That is, the invention disclosed herein detects nucleic acid amplicons.

The detection of amplified nucleic acid for clinical use relies largely on hybridization of the amplified product and detection with a probe labeled with a variety of enzymes and luminescent reagents. U.S. Pat. No. 5,374,524 to Miller, specifically incorporated herein, describes a nucleic acid probe assay that combines nucleic acid amplification and solution hybridization using capture and reporter probes. These techniques require multiple reagents, several washing steps, and specialized equipment for detection of the target nucleic acid. Moreover, these techniques are labor intensive and require technicians with expertise in molecular biology.

The use of probes comprised of oligonucleotide sequences bound to microparticles is well known and illustrated in prior art. The mechanism for attachment of oligonucleotides to microparticles in hybridization assays and for the purification of nucleic acids is also well known. European Patent No. 200133, specifically incorporated herein, describes the attachment of oligonucleotides to water-insoluble particles less than 50 micrometers in diameter used in hybridization assays for the capture of target nucleotides. U.S. Pat. No. 5,387,512 to Wu, specifically incorporated herein, describes the use of oligonucleotide sequences covalently bound to microparticles as probes for capturing PCR amplified nucleic acids. U.S. Pat. No. 5,328,825 to Findlay, specifically incorporated herein, also describes an oligonucleotide linked by way of a protein or carbohydrate to a water-insoluble particle. The oligonucleotide probe is covalently coupled to the microparticle or other solid support. The sensitivity and specificity of all of the above-reference patents is based on hybridization of the oligonucleotide probe to the target nucleic acid.

The use of incorporated non-radioactive labels into the amplification reactions for the detection of nucleic acids is also well known in the art. Nucleic acids modified with biotin (U.S. Pat. No. 4,687,732 to Ward et al.; European Patent No. 063879; both specifically incorporated herein), digoxin (European Patent No. 173251, specifically incorporated herein) and other haptens have also been used. For example, U.S. Pat. No. 5,344,757 to Graf, specifically incorporated herein, uses a nucleic acid probe containing at least one hapten as label for hybridization with a complementary target nucleic acid bound to a solid membrane. The sensitivity and specificity of these assays is based on the incorporation of a single label in the amplification reaction which can be detected using an antibody specific to the label. The usual case involves an antibody conjugated to an enzyme. Furthermore, the addition of substrate generates a calorimetric or fluorescent change which can be detected with an instrument.

Still, the above-described approaches are labor intensive with many steps and washes; require special and costly equipment for the detection of the target nucleic acid; require trained staff; and take several hours to complete. Several patents have issued which deal with automation of the processes of amplification and subsequent detection of the amplicon. These patents use specialized equipment and are still based on the principle of hybridization and immunoassay technology. For example, European Patent No. 320308, specifically incorporated herein, describes a system detecting target nucleic acids amplified by the ligase chain reaction.

Automated approaches eliminate the need for specially trained personnel, however, the cost of the equipment is very high and the possibility of contamination still exists since many samples will be processed by the same equipment. To eliminate the issue of contamination, it is necessary to integrate the three steps outlined above. The self-contained device disclosed herein accomplishes this goal by integrating existing nucleic acid extraction and isothermal amplification technologies with an innovative detection strategy.

The invention described herein provides for the rapid and accurate detection of amplified nucleic acid sequences using a self-contained device. The possibility of contamination is eliminated because of the "throw away" approach described herein. Elimination of cross contamination opens the door to mass screening including automation. The high sensitivity of the analysis allows for the early detection of disease and an opportunity for early treatment. The present invention diagnoses the presence of infectious diseases of genetic, bacterial or viral origin. Analysis by this invention can monitor the efficacy of treatment, for example, to monitor HIV virus in the plasma of patients undergoing therapy. Analysis, according to the invention disclosed herein, is easy, requiring little expertise in the art of molecular biology. The cost is significantly less than other methods currently in use to detect amplified nucleic acids. The time frame for detecting an amplified sequence is reduced drastically. There is no danger from potentially hazardous chemicals. The analysis does not require special waste disposal procedures. The requirements of many washes in an immunometric or hybridization approach are eliminated. The self-contained device does not require special equipment, other than a standard, constant temperature heat block. The low complexity of the device lends itself to "point of care" testing in clinics and physician's offices. The portability of the device provides for "on site" analysis to detect nucleic acid sequences in the areas of forensics, agriculture, environment and the food industry.

Nucleic acid probe technology has developed rapidly in recent years as the scientific community has discovered its value for detection of various diseases, organisms or genetic abnormalities. Amplification techniques have provided the sensitivity to qualitatively determine the presence of even minute quantities of nucleic acid. The drawback to wide spread use of this technology is the possibility of cross contamination of samples since the test is so sensitive. The cost of nucleic acid based testing is high as it requires highly skilled technicians and sophisticated equipment. One method of eliminating the possibility of carry over from one sample to another, is to use a completely enclosed disposable device.

SUMMARY OF INVENTION

This invention is based on a novel concept for a method for detecting specific DNA or RNA sequences. The present invention is defined by a self-contained device integrating nucleic acid extraction, amplification and detection methodologies.

The present invention is a self-contained device that integrates nucleic acid extraction, specific target amplification and detection into a single device, permitting rapid and accurate nucleic acid sequence detection. The present invention is applicable to all nucleic acids and derivatives thereof The present invention is useful to identity specific nucleic acid sequences corresponding to certain diseases or conditions as well as monitoring efficacy in the treatment of contagious diseases, but is not intended to be limited to these uses.

In an embodiment of the invention, the self-contained device comprises a first hollow elongated cylinder with a single closed end and a plurality of chambers therein, a second hollow elongated cylinder positioned contiguously inside the first cylinder capable of relative rotation. Sample is introduced into the second cylinder for extraction. The extracted nucleic acid is bound to a solid phase membrane or silica, and therefore not eluted from the solid phase by the addition of wash buffer. Amplification and labeling takes place in the same cylinder. Finally, the labeled, amplified product is reacted with microparticles conjugated with receptor specific ligands for detection of the target sequence.

In another embodiment of the invention, sample is extracted, amplified and detected in three separate and sequential chambers.

Other features and advantages of the present invention will become apparent from the following detailed description, taken in conjunction with the accompanying figures, that illustrate by way of example, the principles of the instant invention.

The present invention relates generally to a self-contained device integrating nucleic acid extraction, specific target amplification, and detection. This invention relies on the principles of chromatographic nucleic acid extraction from the sample, amplification of specific target nucleic acid sequences resulting in a dual labeled amplification product, ligand-receptor binding, and microparticle technology for detection of amplified nucleic acid. Furthermore, the instant invention may rely on nucleic acid hybridization.

The process according to the present invention is suitable for the determination of all nucleic acid target sequences. The sensitivity and accuracy of this process are improved compared to the processes currently used by those skilled in the art. The invention offers the possibility of contamination free, rapid and reliable determination of the presence of specific amplified target nucleic acids.

BRIEF DESCRIPTION OF THE FIGURES

The file of this patent contains at least one figure executed in color. Copies of this patent with color figure(s) will be provided by the Patent and Trademark Office upon request and payment of the necessary fee.

REFERENCE NUMERALS IN DRAWINGS

Figure 1:
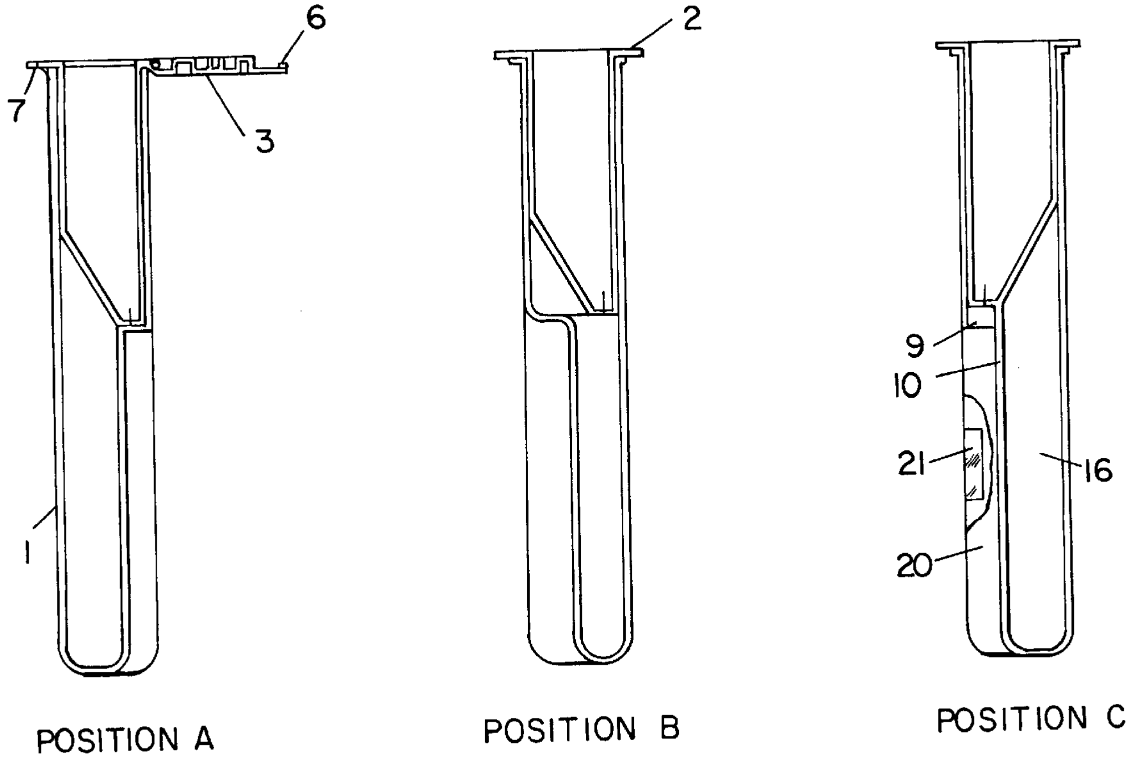
FIG. 1 is a perspective view of a self-contained device integrating nucleic acid extraction, amplification and detection.

1 First hollow elongated cylinder
2 Second hollow elongated cylinder
3 Hinged cover
6 Index pin
7 Index notch
9 Absorbent pad
10 Strip
11 Reaction bead
12 Reaction bead chamber
13 Aperture
14 Living hinge
15 Sealing lip
16 Reservoir
17 Solid surface
18 Knife-edge
19 Foil or foil/polymer membrane
20 Detection chamber
21 Transparent viewing window
22 Porous membrane
23 Silica slurry
24 Colored microparticles
25 Capture zone for target sequence
26 Capture zone for control sequence

DETAILED DESCRIPTION OF THE PREFERRED EMBODIMENT

It is to be understood that both the foregoing general description and the following detailed description are exemplary and explanatory only and are not restrictive of the invention as claimed.

The present invention provides a method of detecting an amplified target nucleic acid sequence that is present in a sample. It is recognized by those skilled in the art that assays for a broad range of target nucleic acid sequences present in a sample may be performed in accordance with the present invention. Samples may include biological samples derived from agriculture sources, bacterial and viral sources, and from human or other animal sources, as well as other samples such as waste or drinking water, agricultural products, processed foodstuff, air, etc. Examples include blood, stool, sputum, mucus, serum, urine, saliva, teardrop, a biopsy sample, an histological tissue sample, a tissue culture product, an agricultural product, waste or drinking water, foodstuff, air, etc. The present invention is useful for the detection of nucleic acid sequences indicative of genetic defects or contagious diseases.

The following definitions will be helpful in understanding the specification and claims. The definitions provided herein should be borne in mind when these terms are used in the following examples and throughout the instant application.

As used herein, the term "target" nucleic acid molecule refers to the nucleic acid molecule that is amplified by the presented methods. The "target" molecule can be purified, partially purified, or present in an unpurified state in the sample.

As used in this invention, the term "amplification" refers to a "template-dependent process" that results in an increase in the concentration of a nucleic acid sequence relative to its initial concentration. A "template-dependent process" is defined as a process that involves the "template-dependent extension" of a "primer" molecule. A "primer" molecule refers to a sequence of nucleic acid that is complementary to a portion of the target or control sequence and may or may not be labeled with a hapten. A "template dependent extension" refers to nucleic acid synthesis of RNA or DNA wherein the sequence of the newly synthesized strand of nucleic acid is dictated by the rules of complementary base pairing of the target nucleic acid and the primers.

The present invention relates to the extraction and amplification of nucleic acids in a chamber of a self-contained device, followed by detection in a another chamber, and collection of waste in, yet, another chamber. The reaction chambers are functionally distinct, sequential and compact. Said chambers deliver precise volumes, dispense reagents and collect waste. All of this occurs in a completely self-contained device with simple, fool proof directions for use as described below.

As illustrated in FIG. 1, an extraction, amplification and detection device consists of a first hollow elongated cylinder 1 having one closed end and an integrally-molded cover 3 hinged to the opposing, open end and a second hollow elongated cylinder 2 that is positioned contiguously inside the first cylinder 1 and capable of relative rotation. The preferred embodiment of the second cylinder 2 is a tapered cylinder terminating with an aperture 13 having a sealing lip 15. The first cylinder 1 further consists of 2 chambers: a reservoir 16 and a detection chamber 20, said detection chamber further consisting of a pad 9 and a strip 10.

The bulk of the device is composed of a material that does not facilitate binding of nucleic acids and proteins. The preferred material is heat and cold resistant material which is light weight, rigid and sturdy. The preferred size is compact enough to fit into conventional size heat blocks, however, the size may be scaled up or down, accordingly. The preferred embodiment inserts the device into a constant temperature environment, such as a heat block, allowing the reactions to proceed at the preferred conditions of constant temperature.

When sample is introduced into the device, nucleic acid extraction and amplification takes place in the second cylinder 2, said first hollow elongated cylinder 2 containing the detection chamber 20 having a means for detection. The reservoir 16 collects the lysis buffer used in the extraction process and subsequent washes.

The second cylinder 2 rotates relative to the first cylinder 1 and locks into position A, position B or position C. At the tapered end of the second cylinder 2, an aperture 13 having a sealing lip 15 enables the second cylinder 2 to engage with either the detection chamber 20 or reservoir 16. The first cylinder 1 contains two chambers, the reservoir 16 and the detection chamber 20. The hinged cover 3 has one indexing pin 6 used for locking the second cylinder 2 in positions A, B and C. The second cylinder 2 is closed to the reservoir 16 in the A, or closed, position. In the B, or open, position, the second cylinder 2 allows flow to the reservoir 16. In the C, or elute, position, amplified nucleic acid target and control are able to wick into the detection chamber 20. The hinged cover 3 also contains a reaction bead 11 within a reaction bead chamber 12. This bead 11 contains the reaction enzymes and other reagents required for the amplification step. The second cylinder 2 contains three notches 7 for indexing with the indexing pin 6 and locking the relative rotation of cylinders 1 and 2.

In position A, the second cylinder 2 is sealed, allowing for the extraction step and the amplification step to take place. In position B, the second cylinder 2 is such that the opening in the second cylinder 2 is not sealed and is over the reservoir 16. In position C, the second cylinder 2 is rotated such that the second cylinder 2 is not sealed and the opening is over an absorbent pad 9 located in the detection chamber 20. The absorbent pad 9 collects the amplified product and wicks the product onto a strip 10 of nylon, nitrocellulose or other suitable material. The strip 10 contains colored microparticles 24 and capture zones for the target 25 and the control 26 sequences. The detection chamber 20 contains a transparent viewing window 21 for observing the results of the reaction.

Figure 2:
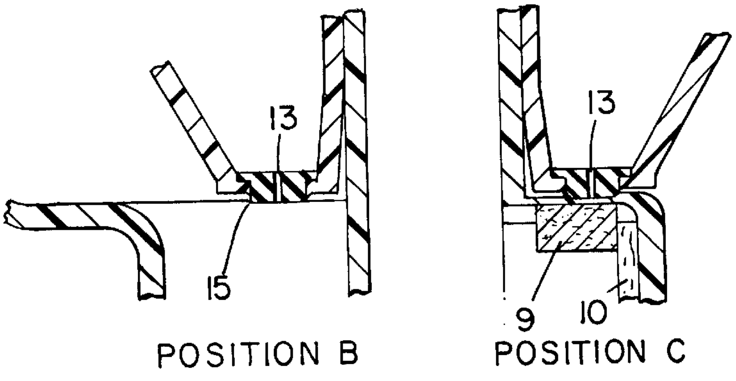
FIG. 2 is a schematic of the preferred sealing mechanism, illustrating each of the three device rotational positions: A) closed; B) open; and C) elute.

FIG. 2 illustrates the preferred embodiment of the sealing mechanism of the device disclosed herein. In open position A, the second cylinder 2 is sealed by a sealing lip 15. The sealing lip 15 is composed of a flexible material that can be compressed when in contact with a solid surface 17 at the top of the first cylinder 1. In close position B, rotation of the second cylinder 2 relative to the first cylinder 1 allow the contents of the second cylinder 2 to flow into the reservoir 16 through a porous membrane 22 in the bottom of the second cylinder 2. In this position, the sealing lip 15 is extended beyond the plane of compression and allows fluid to flow into the reservoir 16. The second cylinder 2 can be rotated relative to the first cylinder 1 into elute position C. In this position, the sealing lip 15 is again extended beyond the plane of compression over an opening containing an absorbent pad 9 and a strip 10 of membrane use for the detection step.

Figure 3:
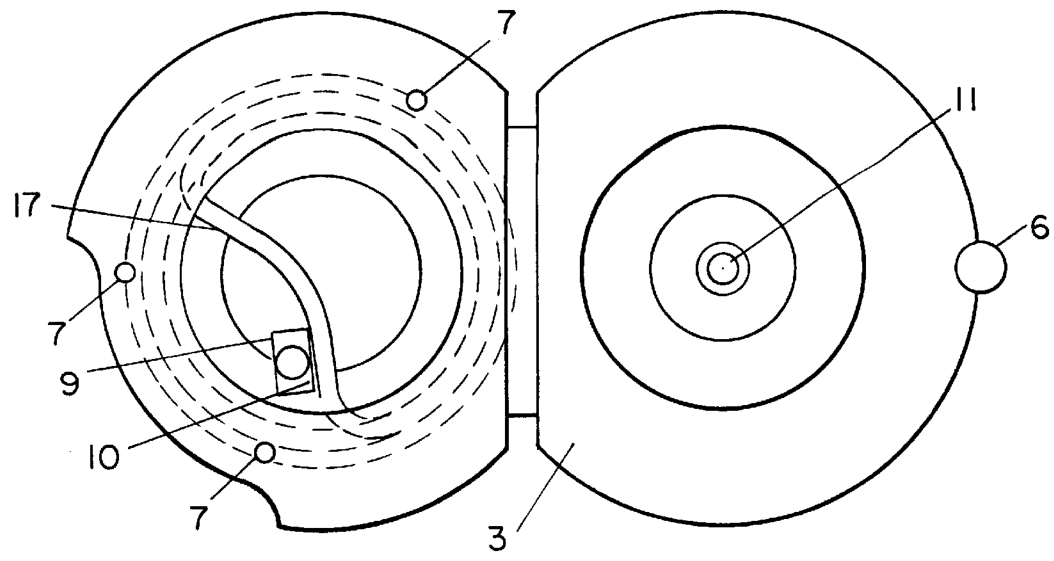
FIG. 3 is a cross-sectional view of the upper and lower bodies of the device, showing the hinged cover in the open position.
Figure 4:
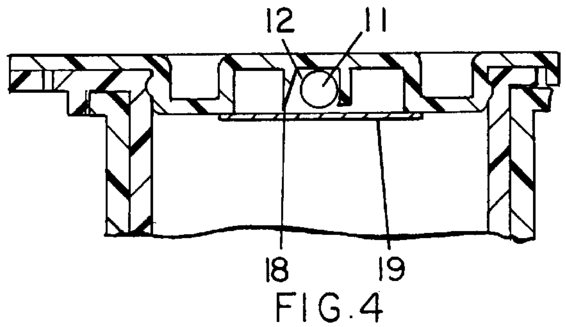
FIG. 4 is a perspective view of the hinged cover and the reaction bead contained within a reaction bead chamber having an integral knife-edge.

A cross-section of the upper 1 and lower 2 body of the device and the hinged cover 3 in the open position is illustrated in FIG. 3. The index pin 6 is located on the hinged cover 3. Three index notches 7 are located on the second cylinder 2. The reaction bead 11 contains lyophilized enzymes and reagents for the amplification reaction. The hinged cover 3 contains a knife-edge 18, which when sufficient pressure is applied thereto punctures a foil membrane 19 releasing the reaction bead 11 into the second cylinder 2, as shown in FIG. 4.

Figure 5:
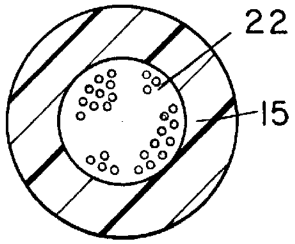
FIG. 5 is a cross-sectional view of the aperture section of the second hollow elongated cylinder.
Figure 6:
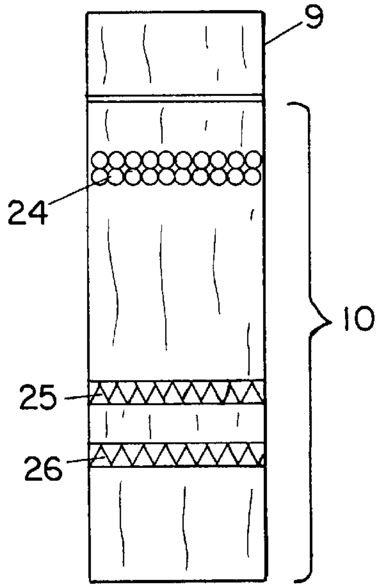
FIG. 6 depicts the relative position of the absorbent pad and strip having microparticles and capture zones.

A cross-section of the bottom of the second cylinder 2 is illustrated in FIG. 5. The sealing lip 15 contains a porous membrane 22 that binds the extracted nucleic acids or a porous membrane 22 that holds a silica slurry 23 in the second cylinder 2. A strip 10 containing a region with immobilized colored microparticle 24 and two capture zones 25, 26 is depicted in FIG. 6. The microparticles 24 are coated with a receptor that is specific to the target and the control sequence. Target sequence capture zone 25 contains receptors specific for haptens on the target sequence and control sequence capture zone 26 contains receptors specific for haptens on the control sequence.

The following examples serve to explain and illustrate the present invention. Said examples are not to be construed as limiting of the invention in anyway. Various modifications are possible within the scope of the invention.

EXAMPLE 1

Sample Flow Through the Preferred Embodiment of a Self-Contained Device

Figure 7:
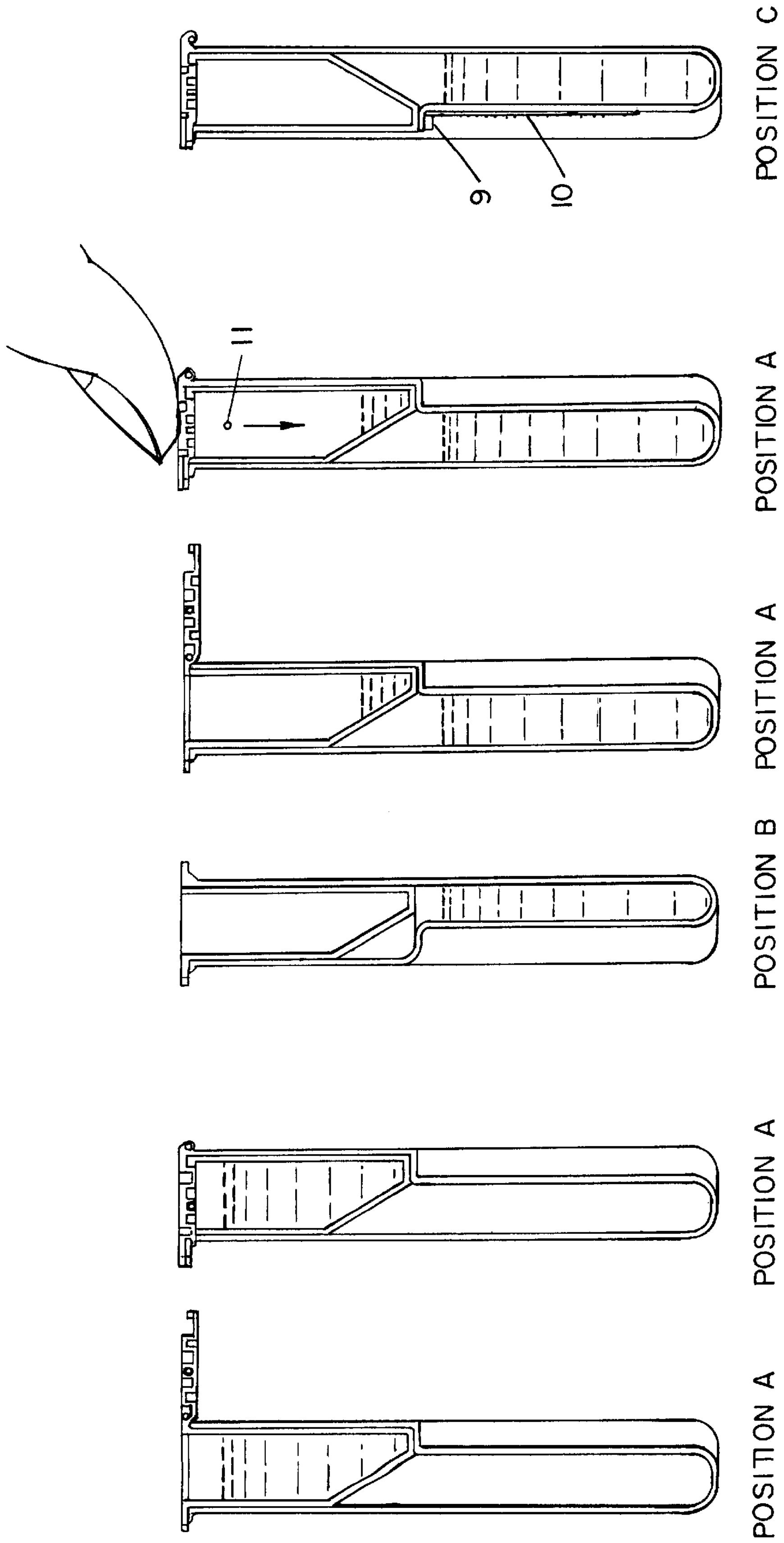
FIG. 7 depicts a sequential perspective view illustrating the operating sequence of the self-contained device.

The preferred embodiment of the device disclosed herein is defined by two hollow elongated cylinders, a first cylinder having a closed end, as illustrated in FIG. 1, for the extraction, amplification and detection of nucleic acid sequences. In the close position A, sample is introduced into the second cylinder 2. The second cylinder 2 contains dry lysing reagents for extraction of nucleic acids. The sample provides the liquid that resuspends the lysing reagents. After a brief incubation period with the cover 3 closed, the second cylinder 2 is rotated into open position B. The extracted nucleic acid remains in the upper chamber bound to the porous membrane 22 or the silica slurry 23, while the liquid flows into the reservoir 16. In this position, several washes of buffer or water follow. Next, the second cylinder 2 is rotated into close position A such that the second cylinder 2 is sealed, water is added and the cover closed. When sufficient pressure is applied to the hinged cover 3, the reaction bead 11 is released from the reaction bead chamber 12 and added to the second cylinder 2 by breaking the foil membrane 19 with the knife-edge 18. The reaction bead 11 carries the enzymes necessary for amplification, which are resuspended in the water and amplification takes place on the membrane 22 or silica slurry 23 containing the extracted nucleic acids. After an appropriate incubation period, the second cylinder 2 is rotated relative to the first cylinder 1 into elute position C. The amplification reaction mixture is able to enter the detection chamber 20 as it is absorbed onto the pad 9. When the pad 9 absorbs a sufficient amount of liquid, the reaction mixture is wicked up the strip 10. On the strip, the colored microparticles 24 bind to haptens resulting from the amplification reaction and travel to the capture zone on the membrane where they form a visible line of detection if the target sequence is present and for the control sequence. The line of detection is viewed from the transparent viewing window 21. See FIG. 7.

The second cylinder 2 has a capacity of 0.001 to 25 ml. Sample is whole blood, sputum, serum, plasma, urine, fecal matter, a tissue, part of an organ or any other source that may contain the target nucleic sequence. Sample is from humans, plants or animals and may be environmental in nature.

The method and apparatus disclosed herein provides for extremely rapid, economical nucleic acid detection. Further, this self-contained device significantly reduces the risk of cross contamination in that neither amplification reagents nor amplicons are manipulated. The minimal additional instrumentation required, a standard heat block, and simplicity of the protocol, enable the test to be performed easily, anywhere and with a minimum amount of technical experience.

EXAMPLE 2

Microparticle Selection

The preferred microparticles utilized in this invention are composed of polymeric materials such as latex polyethylene, polypropylene, polymethylmethacrylate or polystyrene. However, a variety of other synthetic or natural materials may also be used in the preparation of the microparticles, for example, silicates, paramagnetic particles and colloidal gold. The usual form of microparticles possesses surface sulfate charge groups that can be modified by the introduction of functional groups such as hydroxyl, carboxyl, amine and carboxylate groups. The functional groups are used to bind a wide variety of ligands and receptors to the microparticles. These groups are selected on the basis of their ability to facilitate binding with the selected member of the ligand-receptor pair, either by covalent binding or adsorption. The preferred method of attachment of the receptor to the microparticles is covalent binding.

The size of the microparticles used in this invention is selected to optimize the binding and detection of the labeled amplicons. Microparticles are available in a size range of 0.01–10.0 μm in diameter. The preferred diameter for this embodiment of the invention is a range of 0.01–1.0 μm, specifically not excluding the use of either larger or smaller microparticles as appropriately determined. The microparticles are activated with a suitable receptor for binding to the target ligand. The preferred microparticle in the present invention is composed of latex containing a colored dye.

In the present invention, microparticle bound receptors are specific for discreet haptens located on the ends of amplified nucleic acid sequences. The receptors must be capable of binding to their specific binding partner (hapten) and, further, changing the derivatized haptens from the preferred biotin and digoxigenin necessitates a change in the receptors. Conjugation of the receptors to the microparticle is accomplished by covalent binding or, in appropriate cases, by adsorption of the receptor onto the surface of the microparticle. Techniques for the adsorption or covalent binding of receptors to microparticles are well known in the art and require no further explanation.

In order to prepare the anti-digoxigenin coated microparticles, 0.25–1.0 mg/ml of anti-digoxigenin Fab is incubated with a suspension containing a final concentration of 1.0% microparticles/ml. The microparticles and digoxigenin Fab are allowed to react for 15 minutes prior to treatment with activating agent for covalent binding. The microparticles are treated with EDAC (1-ethyl-3-(3-dimethylaminopropyl) carbodiamide) at a final concentration of 0–2.5 mM. The Fab and microparticles are mixed and incubated at room temperature for one hour. Unbound Fab is removed by successive washes and the coated microparticles are resuspended in storage buffer.

Lateral flow assays are performed on nylon or nitrocellulose membranes spotted with capture zones of 1.0 μl streptavidin at concentrations between 0.0 and 1.0 mg/ml.

EXAMPLE 3

Amplification

The present invention employs a variety of different enzymes to accomplish amplification of the target nucleic acid sequence, for example, polymerases and ligases. Polymerases are defined by their function of incorporating nucleoside triphosphates to extend a 3' hydroxyl terminus of a "primer molecule." As used herein, a "primer" is an oligonucleotide, that when hybridized to a target nucleic acid molecule, possesses a 3' hydroxyl terminus that can be extended by a polymerase and a hapten label at or near the 5' terminus. For a general discussion concerning polymerases, see Watson, J. D. et al., (1987) *Molecular Biology of the Gene,* 4th Ed., W. A. Benjamin, Inc., Menlo Park, Calif. Examples of polymerases that can be used in accordance with the methods described herein include, but are not limited to, *E. coli* DNA polymerase I, the large proteolytic fragment of *E. coli* polymerase I, commonly known as "Klenow" polymerase, Taq-polymerase, T7 polymerase, T4 polymerase, T5 polymerase and reverse transcriptase. The general principles and conditions for amplification of nucleic acids using polymerase chain reaction, as discussed supra, are well known in the art.

EXAMPLE 4

Isothermal Amplification Approach to Detection with Labeled Amplified Target Sequence Using NASBA The preferred embodiment for amplification using this invention is an isothermal reaction such as NASBA (U.S. Pat. No. 5,130,238, specifically incorporated herein) or strand displacement assay (SDA)(Walker et al. (1992) PNAS 89:392, specifically incorporated herein). The primary product of the NASBA reaction is single strand RNA. The NASBA reaction utilizes a primer containing a T7 polymerase promoter. Following T7 transcription, up to 100 copies of target RNA are produced. These copies are the same sequence as the original target RNA. They serve as templates, thus, starting the cycle again and resulting in up to a billion fold amplification of the original template.

Figure 8:
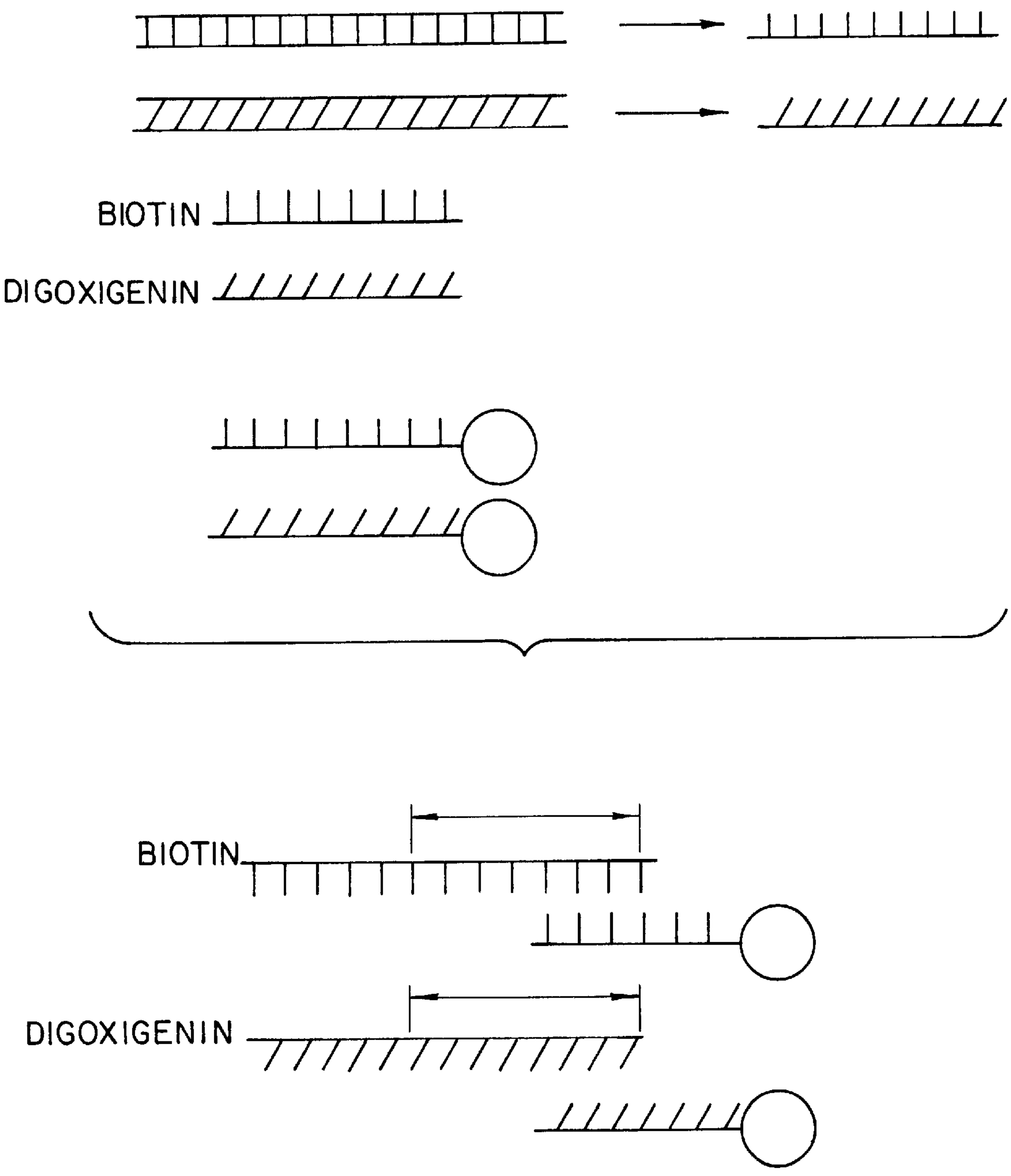
FIG. 8 illustrates the reagents and their perspective interaction in the amplification chamber of the device in an SDA strategy.
Figure 9:
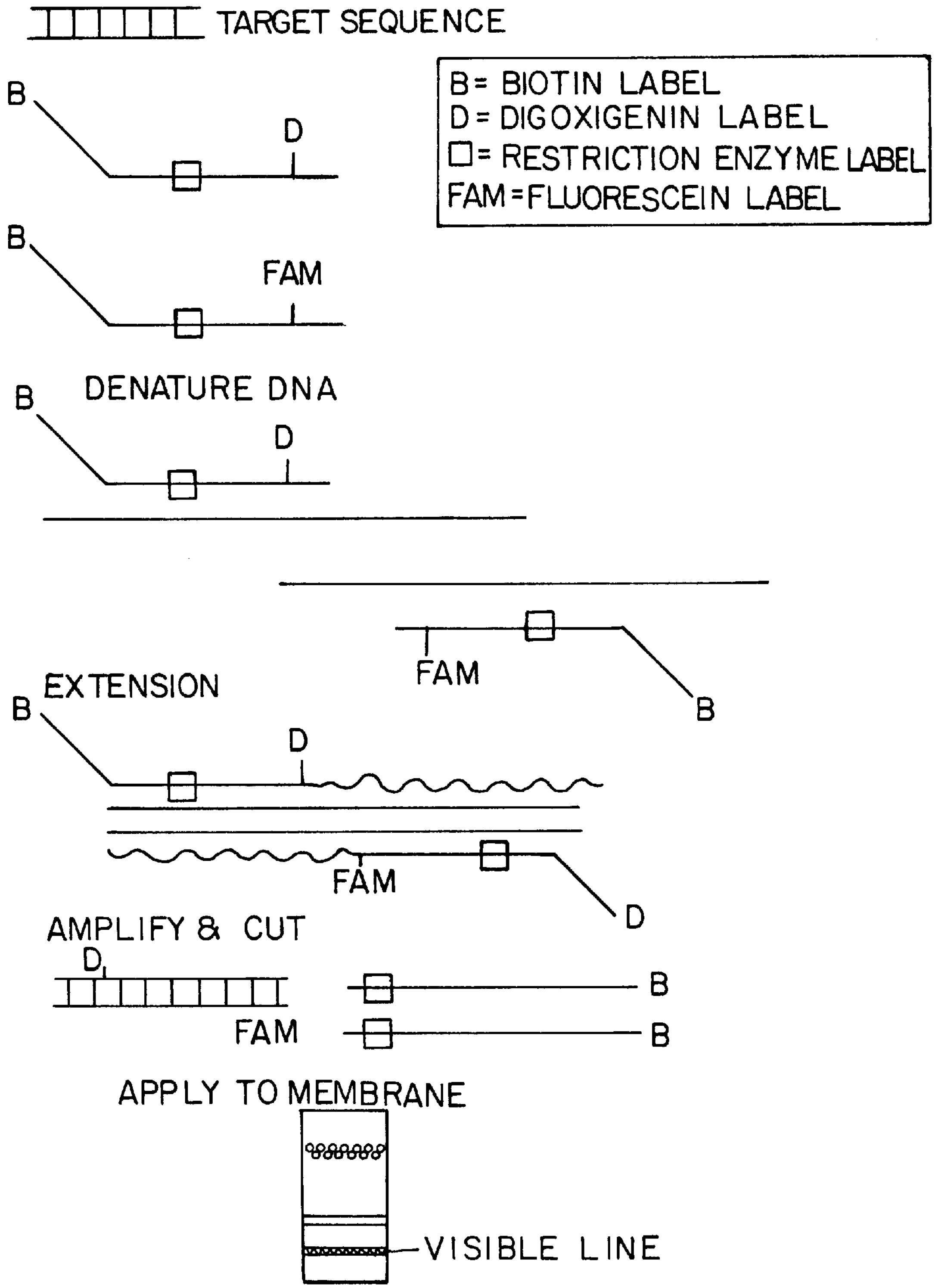
FIG. 9 depicts reagents and their respective interactions in an alternate SDA strategy.

In order to incorporate NASBA into the device disclosed herein, probes that allow the formation of a bifunctionally haptenized amplification product have been designed. For NASBA there are two possible strategies: 1) design amplification primers that are haptenized; and 2) use two haptenized capture oligos which bind to the product RNA. See, for example, FIGS. 8 and 9. The model system chosen is to the HIV POL gene.

In the instant NASBA haptenization strategy, the T7NASFAM haptenization primer, containing a T7 transcriptase promoter and an attached fluorescein, binds to the target RNA. A reverse transcriptase transcribes a DNA copy of the RNA, as illustrated in example B of FIG. 14. The original RNA strand is digested by RNase H. A reverse haptenization primer, P2NASBIO with attached biotin binds to the antisense DNA and is extended by the DNA polymerase activity of the reverse transcriptase. The haptenized primers are as follows:

```
T7NASFAM (T7-PROMOTER PRIMER):
5'-FLUORESCEIN
-AATTCTAATACGACTCACTATAGGGTGCTATGTCACTTCCCCTTGGTTCTCT-3' SEQ ID NO:1

P2NASBIO (REVERSE PRIMER):
5'BIOTIN-AGTGGGGGGACATCAAGCAGCCATGCAAA-3'              SEQ ID NO:2
```

Figure 14:
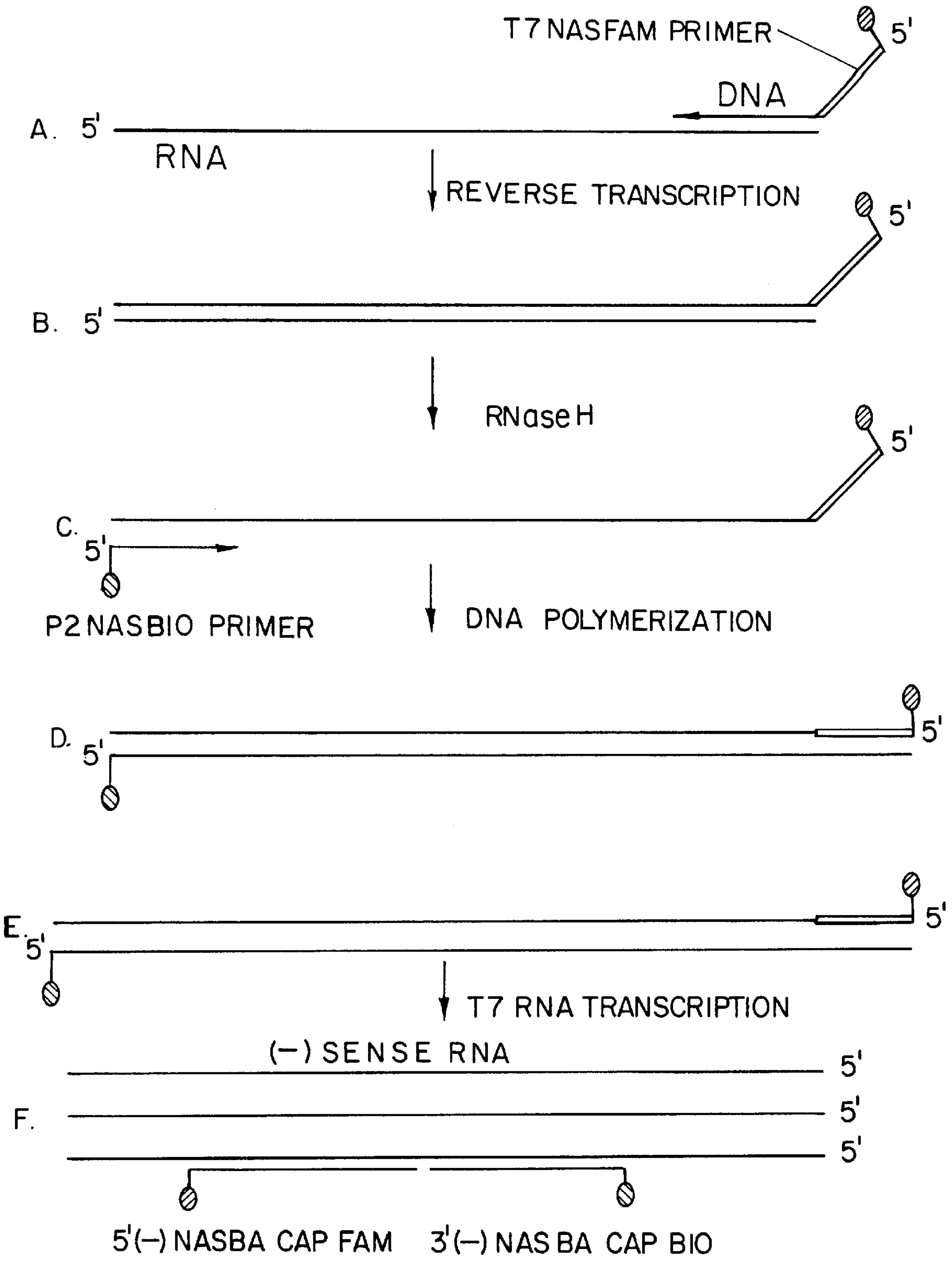
FIG. 14 depicts a NASBA strategy.

The resulting double-stranded bi-haptenization DNA intermediate is illustrated in example D of FIG. 14. This complex gives signal in lateral flow or slide agglutination.

T7 RNA polymerase binds to the promoter region to manufacture many copies of a minus-sense RNA, as shown in example F of FIG. 14. This RNA contributes to the manufacture of the DNA intermediate by similar means. Two capture oligos, each having one hapten of either fluorescein or biotin, bind to the (−)sense RNAs giving bifunctional haptenized complexes. These complexes give signal in lateral flow or slide agglutination. The haptenized capture oligos designed to bind to the minus-sense RNA product are:

```
5C(-)NASBA:
5'FLUORESCEIN-TGGCCTGGTGCAATAGGCCC-3'  SEQ ID NO:3

3C(-)NASBA:
5'CCCATTCTGCAGCTTCCTCA-BIOTIN-3'       SEQ ID NO:4
```

EXAMPLE 5

Isothermal Amplification Approach to Detection with Bifunctionally Labeled Amplified Target Sequence Using Strand Displacement Assay The instant strand displacement assay (SDA) is an example of an isothermal amplification that can be detected by using microparticles and bifunctionally labeled product. SDA technology is described in U.S. Pat. No. 5,455,166 to Becton Dickinson and Company, specifically incorporated herein.

SDA is isothermal amplification based on the ability of a restriction enzyme to nick the unmodified strand of a hemiphosphorothioate from of its recognition site and the ability of DNA polymerase to initiate replication at the nick and displace the downstream non-template strand. Primers containing recognition sites for the nicking restriction enzyme bind to opposite strands of target DNA at positions flanking the sequence to be amplified. The target fragment is exponentially amplified by coupling sense and antisense reactions in which strands displaced from the sense reaction serve as a target for the antisense reaction and vice versa.

This set of experiments is conducted with composite extension primers that are labeled with biotin, fam or digoxigenin. Bumper primers are the same sequence as provided by Becton Dickinson and Company (Franklin Lakes, N.J.). The sequences of the target, the bumper primer and the composite extension primer are as follows:

Membrane used for this procedure is nitrocellulose, purchased from Millipore Corporation, Bedford, Mass. A stripe of streptavidin at a concentration of 1 mg/ml is applied at a rate of 1 μl/cm via a linear reagent striper (IVEK Corporation, No. Springfield, Vt.) 1 cm from the bottom edge of the membrane. After application of the streptavidin, the membrane is allowed to dry and then blocked for non-specific binding by 0.5% casein in 100 mM Tris, pH 7.4. The membranes are washed twice with water ($ddH_2O$) and allowed to dry. Next, 3 μl of anti-S1 (complementary to S1 without the biotin label) and/or S2 primer (complementary to S2 without the dig or fam label) is spotted onto a second membrane. This membrane is sandwiched onto the first membrane in order to capture free primers that compete with the product for the microparticles or streptavidin capture zone. The microparticles are prepared as outlined supra in Example 2 with either anti-digoxigenin Fab or anti-fam monoclonal IgG. The microparticles are diluted 1:2 with a 35% sucrose solution and 3 μl applied directly to the membrane and dried.

Figure 11:
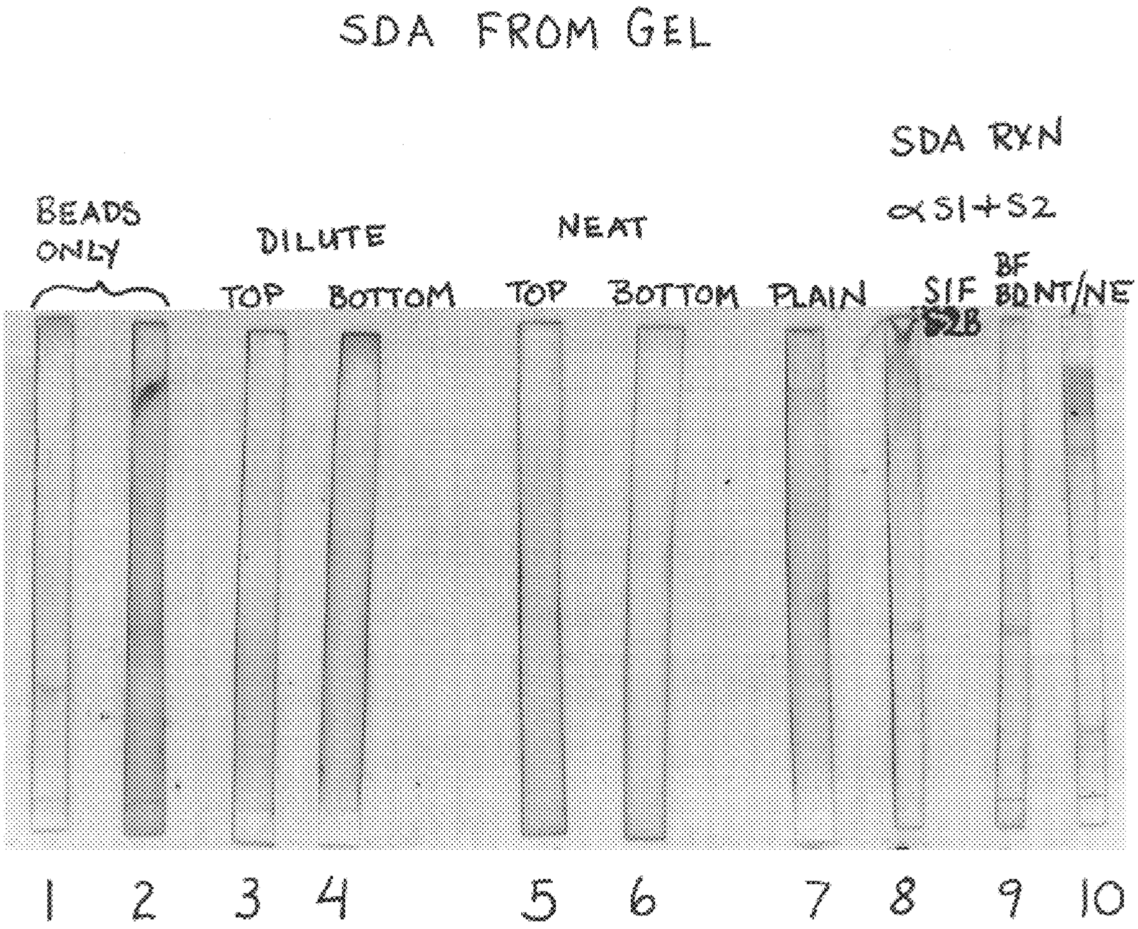
FIG. 11 illustrates the detection results of isothermal amplification and detection with bifunctionally labeled amplified target sequence using strand displacement assay.

The reaction product (10 μl) is added to 45 μl SDA buffer, then applied (50 μl) to the previously striped membrane. Application of the sample requires the bifunctionally labeled product and the competing primers to pass through the anti-primer coated membrane and the dried microparticles. When the target is present, there is a visible line on the membrane. When the target is not present, there is absence of a visible line. The results of one such experiment are shown in FIG. 11.

EXAMPLE 6

Inhibition Assay: Loss of Visible Signal on Lateral Flow Membrane

Figure 10:
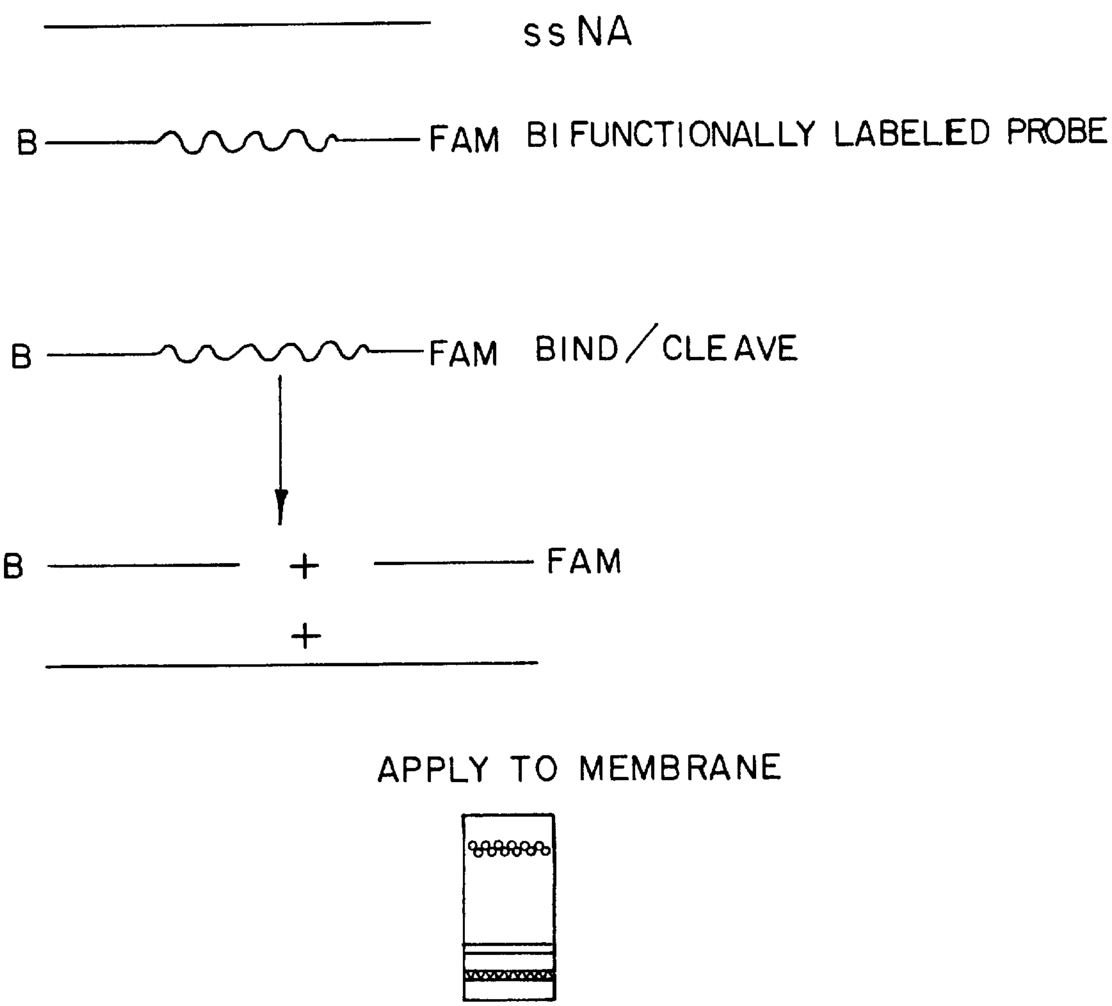
FIG. 10 depicts the reagents and their respective interactions in a cycling probe assay.

Cycling probe technology involves a nucleic acid probe that incorporates DNA-RNA-DNA sequences designed to hybridize with the target sequences. See, for example, FIG. 10. The probes are bifunctionally labeled with biotin and fam. If the probes hybridize with the target generating double stranded nucleic acid, RNase H in the reaction buffer cleaves the probes. This cleavage results in loss of signal when applied to a membrane containing a capture zone of streptavidin and anti-fam coated, colored microparticles. If the target is not present, there is a visible line on the membrane.

```
Bumper Primers:
B1: 5'-CGATCGAGCAAGCCA                                      SEQ ID NO:5

B2: 5'-CGAGCCGCTCGCTGA                                      SEQ ID NO:6

Composite extension primers:
S1: 5'-fam/dig-ACCGCATCGAATGCATGTCTCGGGTAAGGCGTACTCGACC  SEQ ID NO:7

S2: 5'-biotin-CGATTCCGCTCCAGACTTCTCGGGTGTACTGAGATCCCCT   SEQ ID NO:8

Target sequence:
5'TGGACCCGCCAACAAGAAGGCGTACTCGACCTGAAAGACGTTATCCACCAT    SEQ ID NO:9

ACGGATAGGGGATCTCAGTACACATCGATCCGGTTCAGCG
```

The reaction is set up per the thermophilic Strand Displacement Amplification (tSDA) protocol developed by Becton Dickinson and Company. The target organism is *Mycobacterium tuberculosis*. For pilot studies, an artificial target template consisting of the 91nt sequence of the *M tuberculosis* genome, defined by the Becton Dickinson outer (bumper) primers, is used. Amplification conditions used are identical to those used by Becton Dickinson for tSDA.

The specific probe and target employed in the instant example have been designed by ID Biomedical Corporation for use in detecting *Mycobacterium tuberculosis*. The probe is a chimeric construct containing both DNA and RNA sequences with labels on the 5' (fam) and the 3' (biotin) ends of the DNA portion of the probe. The binding of the probe to a single strand of target generates double stranded nucleic acid which is cleaved with RNase H, thus, eliminating the bifunctionality of the probe. The sequence of the probe is described below:

```
SEQ ID NO:10
FARK2S3B probe
5'-fam AAA GAT GT agag GGT ACA GA-3'biotin
(lower case indicates deoxyribonucleoside bases)

SEQ ID NO:11
The sequence of the target is described below:
ARK2-T synthetic target
5'-AAT CTG TAC CCT CTA CAT CTT TAA-3'
```

The reaction is completed following the protocol provided by ID Biomedical Corporation. Membrane used for this procedure is nitrocellulose, purchased from Millipore Corporation, Bedford, Mass. A stripe of streptavidin at a concentration of 1 mg/ml is applied at a rate of 1 μl/cm via a linear reagent striper (IVEK Corporation, No. Springfield, Vt.) 1 cm from the bottom edge of the membrane. After application of the streptavidin, the membrane is allowed to dry and then blocked for non-specific binding by 0.5% casein in 100 mM Tris, pH 7.4. The membranes are washed twice with water (dd$H_2O$) and allowed to dry. The microparticles used are prepared as outlined supra in Example 2, replacing anti-digoxigenin Fab with anti-fam monoclonal IgG.

Figure 12:
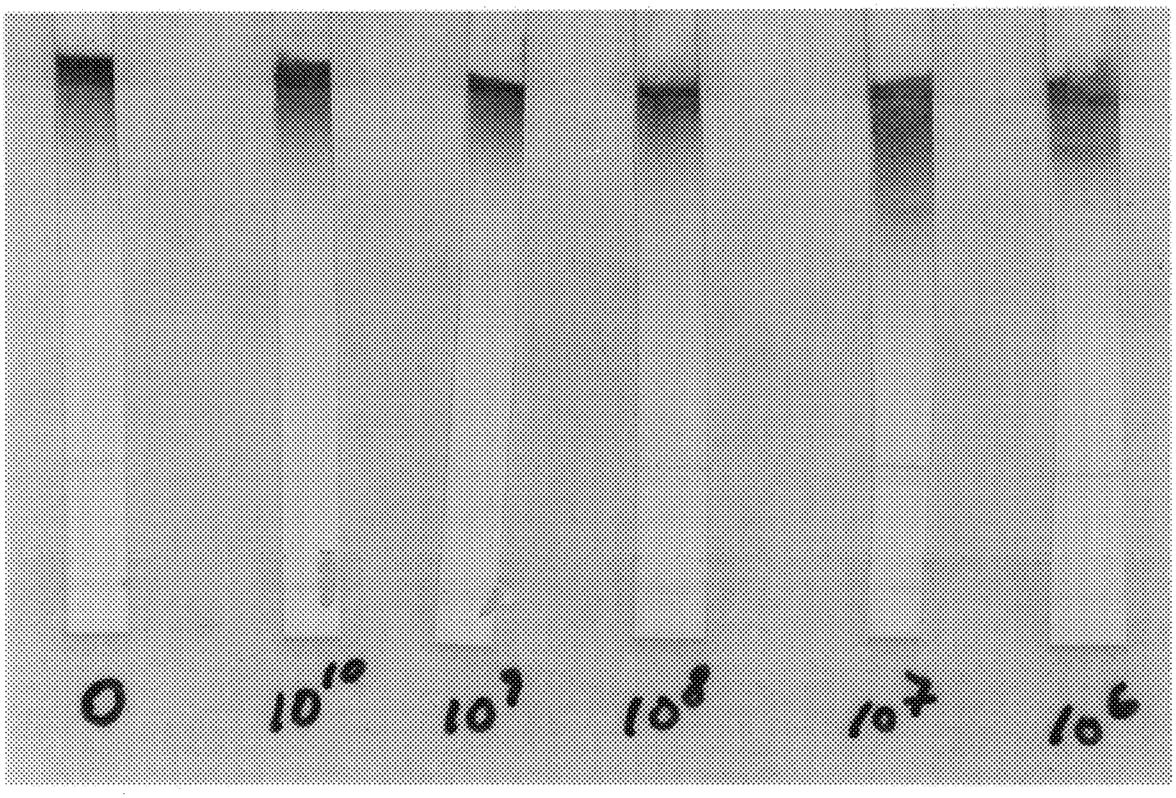
FIG. 12 shows the detection results of a lateral flow assay.

The reaction product (10 μl) is added to 5 μl of 0.1% anti-fam coated microparticles (0.1%) and 35 μl of water, then applied (50 μl) to the previously striped membrane. The binding of the probe to the target followed by cleavage of the probe by RNase H, results in loss of the bifunctionality of the probe. When the target is present, the absence of a visible line on the membrane exists. When the target is not present, the bifunctionally labeled probe is able to bind the anti-fam coated microparticles and the streptavidin bound to the membrane, resulting in a visible line. The results of one such experiment are shown in FIG. 12.

With amplification, certain specimens are inhibitory to the amplification reaction providing false-negative results. To avoid this problem, a positive control—a control nucleic acid with primer recognition sequences attached to a totally irrelevant nucleic acid sequence—is incorporated. This positive control primer is a component of the nucleic acid extraction reagents in second cylinder of the device, thus, controlling for sample extraction and delivery as well as detecting amplification failure. The preferred embodiment of the positive control is a lambda DNA sequence. The control nucleic acid is extracted and amplified along with the target nucleic acid and is detected by a line of immobile anti-digoxigenin beads on the detection solid phase.

The target oligonucleotide primer and the control oligonucleotide primer used in this invention contain at least one hapten as label which does not participate in the priming reaction. The hapten is bound to at least one position of the nucleic acid primer. For the derivatization of nucleic acid primers, various methods can be employed. See, Sambrook supra. The incorporation of the hapten can take place enzymatically, chemically or photochemically. The hapten can be derivatized directly to the 5' end of the primer or contain a bridge 1 to 30 atoms long. In the preferred embodiment, the bridge is linear. However, in an alternate embodiment, the bridge consists of a branched chain with a hapten molecule on at least one of the chain ends. By means of the presence of several hapten molecules on the ends of a branched chain, the detection sensitivity is increased. The preferred haptens for the present invention are biotin and digoxigenin, however, other haptens having a receptor as specific binding agent available are suitable, for example, steroids, halogens and 2,4 dinitrophenyl.

EXAMPLE 7

Detection of Bifunctionally Labeled Amplified Product

Membrane used for this procedure is nitrocellulose, purchased from Millipore Corporation, Bedford, Mass. A stripe of streptavidin at a concentration of 1 mg/ml is applied at a rate of 1 μl/cm via a linear reagent striper (IVEK Corporation, No. Springfield, Vt.) 1 cm from the bottom edge of the membrane. After application of the streptavidin, the membrane is allowed to dry and then blocked for non-specific binding by 0.5% casein in 100 mM Tris, pH 7.4. The membranes are washed twice with water (dd$H_2O$) and allowed to dry.

Figure 13:
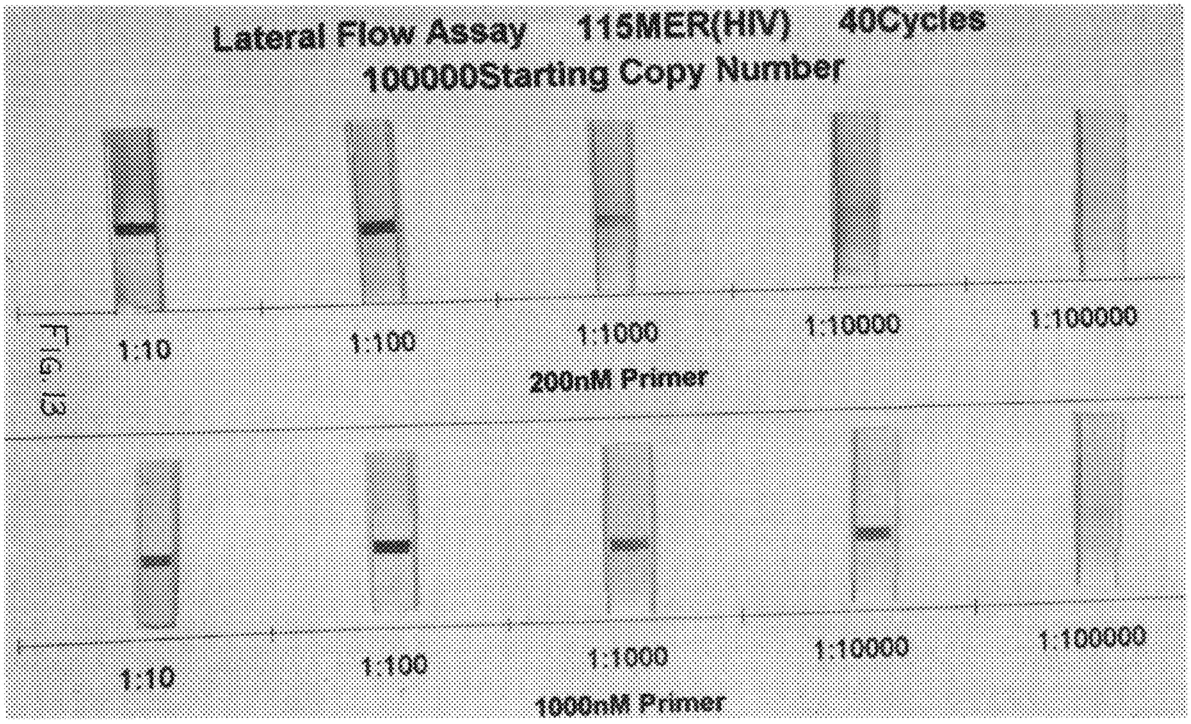
FIG. 13 shows the detection results of an alternate lateral flow.

The amplification product is added to the membranes with colored receptor coated beads at dilutions of 0.001–1.0% microparticles/ml. This mixture is allowed to wick up the membrane. Positive reactions result in a colored line where the capture material is applied. Amplification reactions without the target sequence added to the reaction serve as negative controls. The results of one of these experiments are illustrated in FIG. 13.

If the target and control nucleic acid sequence are present, the receptor bound microparticles interact with hapten(s) to capture the amplified nucleic acid. The result, a line of dyed particles visible on the membrane for the target and for the control nucleic acids. If the target is not present, the dyed particles are not captured and are not visible. When the result of the analysis is negative, the control nucleic acid sequences must be visible indicating that the extraction and amplification were performed correctly.

EXAMPLE 8

Detection by Amplification with a Single Labeled Primer Followed by Hybridization with a Probe That Contains a Single Label The target nucleic acid sequence is amplified by PCR using 200–1000 mM primer concentration, GeneAmp EZ rTth RNA PCR kit (Perkin Elmer Corp., Alameda, Calif.) and $10^6$ copies/ml of the target HIV RNA sequence. Forty PCR cycles, each cycle being 60° C. for 15 minutes, 95° C. for 15 seconds, and 55° C. for 60 seconds, are run.

The sequences of the primers is as follows:

```
SEQ ID NO:12
SK38 Dig Primer
5'-DIG ATA ATC CAC CTA TCC CAG TAG GAG AAA T-3'

SEQ ID NO:13
SK39 Primer
5'-TT TGG TCC TTG TCT TAT GTC CAG AAT GC-3'
```

Specific PCR reaction conditions are described below:

| Reagent | Final conc. |
|---|---|
| 5X EZ Buffer | 1X |
| $Mn(OAc)_2$ | 3 mM |
| rTth polymerase | 5 U |
| dntp's | 240 μM each |
| SK38 | 1 μM |
| SK39 | 1 μM |

rTth DNA Polymerase from Perkin Elmer N808-0097

The SK38 Dig—SK39 amplicon (5 μl) is incubated with 5 μl of 25 μM (125 pmol) SK39 biotin at 95° C. for 1 minute, and then 55° C. for 1 minute. The amplicon bound to the anti-digoxigenin microparticles wicks through the membrane to the streptavidin line and is captured by the interaction of biotin and streptavidin. The result is a visible line of colored microparticles.

Figure 15:
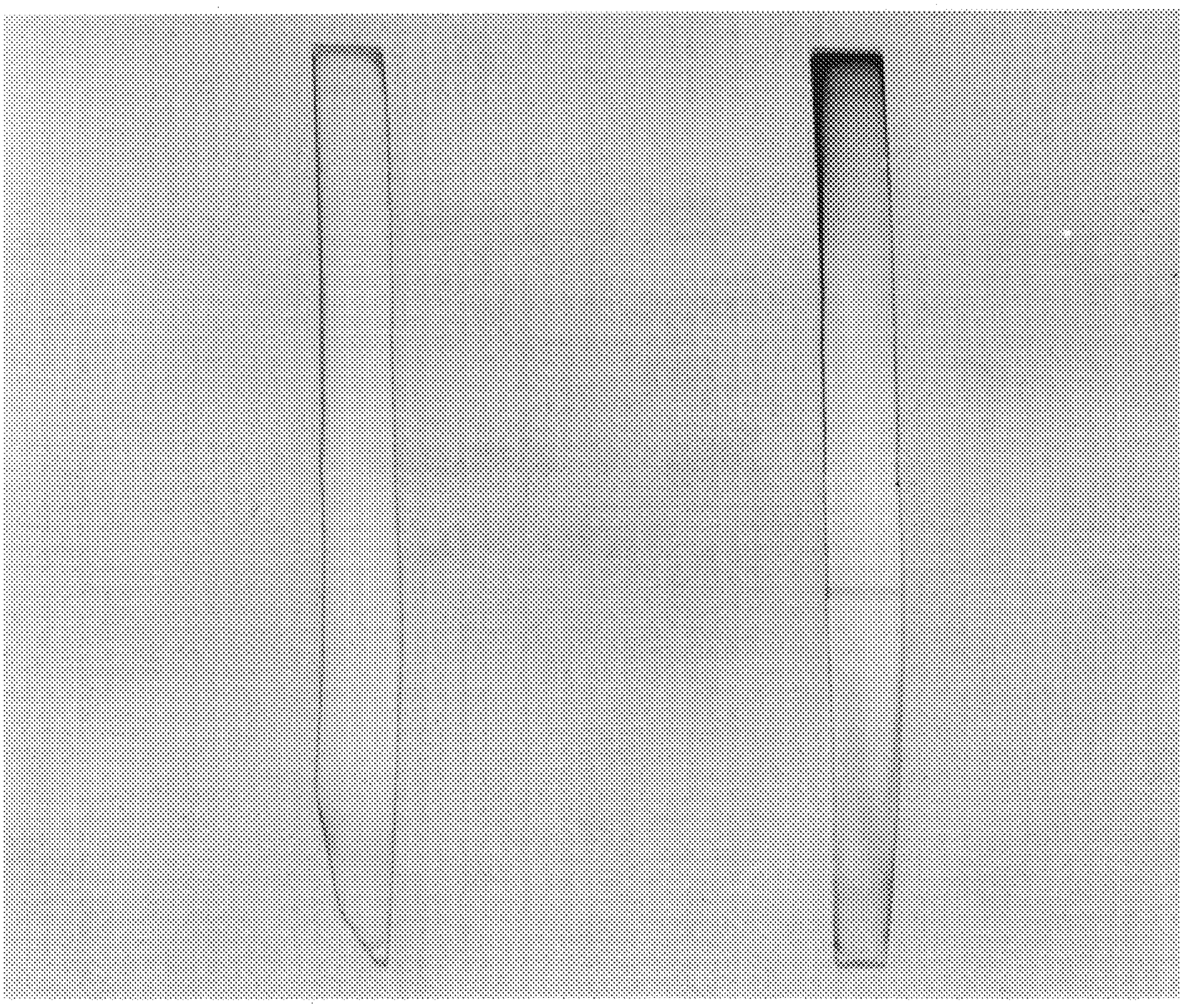
FIG. 15 shows the results of detection by amplification with a single labeled primer followed by hybridization with a probe containing a single label.

In the negative control, the procedure is performed as described above, but without the addition of the target sequence. Without the presence of the target sequence in the amplification reaction, the bifunctionally labeled amplicon is not generated and the visible line of detection is not present. The results of one such experiment are shown in FIG. 15.

EXAMPLE 9

Alternate Embodiment of a Self-Contained Device

Sample is introduced into an extraction chamber for extraction of nucleic acid. This chamber incorporates a nucleic acid extraction/solid phase nucleic acid binding protocol providing a rapid method of nucleic acid purification. The preferred extraction method makes use of chaotropic agents such as guanidine isothiocynate to disrupt the cell membranes and extract the nucleic acid. Proteins are degraded by proteinases. The extracted nucleic acid binds to a solid phase membrane in the extraction chamber. The nucleic acid is eluted from the solid phase by the addition of elution buffer. The design of a fitting between the solid phase membrane and a seal prevents waste from entering the amplification chamber.

After the sample is added to the extraction chamber, a supply assembly unit locks onto the top of a processor assembly unit by connecting a first and a second fitting. Following a 10–15 minute incubation allowing nucleic acid extraction, the first of four plungers is depressed. Air in a compartment forces the extraction mixture past the solid phase membrane binding the nucleic acid. The filtrate is collected in a waste chamber. Depression of the second plunger forces a wash buffer stored in a wash buffer compartment across the solid phase membrane and filtrate passes to the waste chamber. The seal located directly below the solid phase membrane is disposed at an angle to aid in efficient collection of the waste. Depressing the third plunger forces air stored in a compartment across the solid phase membrane, insuring that all of the wash buffer is removed. The processor assembly unit twists, simultaneously breaking the seal and closing off a waste chamber conduit. Depressing the fourth plunger delivers an elution buffer stored in a compartment for elution of the nucleic acid from the solid phase and delivers a volume of nucleic acid into an amplification chamber.

In the alternate embodiment, the amplification chamber contains the reagents for amplification and hybridization. In additional alternative embodiments, reagents for amplification and hybridization are in separate chambers. This process is characterized in that the sample is treated, after extraction, with two distinct labeled oligonucleotides primers. The sequence of the first primer is complementary to a partial sequence of a strand of the target nucleic acid and is labeled with hapten, for example, biotin. The sequence of the second primer is complementary to a partial sequence of the control nucleic acid and labeled with a second hapten, for example, digoxigenin. Either primer may contain a promoter region. Subjecting the mixture to amplification, preferably isothermal amplification, results in hapten labeled target and control nucleic acid. These labeled, amplified nucleic acid sequences react with oligonucleotides conjugated to microparticles of suitable color and diameter for detection. The microparticles are conjugated with an oligo specific for binding nucleic acid sequence on the target. The microparticles are conjugated with an oligo specific for binding nucleic acid on the control. The resulting microparticles, bound by hybridization to the amplicons, are detected in the detection chamber.

EXAMPLE 10

Extraction of Nucleic Acids with Quanidinium Thiocyanate onto Glass (Silica Dioxide) and Subsequent Amplification Without Elution from Silica Dioxide A column was constructed using Ansys 0.4 mm membrane as filter to contain the silica dioxide and a syringe apparatus to pull buffer through the column in approximately 15 seconds. 50 $\mu$l serum, 2 $\mu$l SiO2 (0.5 mg/$\mu$l), and 450 $\mu$l GuSCN lysis buffer are mixed by vortexing and then incubated at room temperature for 10 minutes. The specific lysis buffer for the instant set of experiments contains 14.71 g GuSCN (4M final), 0.61 ml "Triton X-100", 5.5 ml 0.2M EDTA pH 8.0 and is q.s. to 31.11 ml with 0.1M Tris-HCl pH 6.4. The silica dioxide is washed twice with 500 $\mu$l 70% ETOH.

Next, the filter with SiO2 is removed from the column and the SiO2 washed off of the membrane using 20 $\mu$l water ($ddH_2O$). 5 $\mu$l silica dioxide slurry is added to a PCR reaction using standard protocol for HIV model system, as detailed supra in Example 8.

The instant invention provides a rapid, simple and accurate method of detecting amplified target nucleic acid sequences with a self-contained device. Sensitivity and specificity of the assay are based on labeling of the target, by incorporating label or by subsequent hybridization of labeled probed, during the amplification process. The method does not require costly and sophisticated equipment or specially trained personnel, nor does it pose any health hazard.

While the above description contains many specificities, these should not be construed as limitations on the scope of the invention, but rather an exemplification of the preferred embodiment thereof. Many other variations are possible, such as amplifying several target samples in the same reaction mixture, utilizing newly discovered polymerases and ligases, etc. Thus, the scope of the invention should be determined by the appended claims and their legal equivalents, rather than by the example given.

We claim:

1. A self-contained device for the extraction, amplification and detection of nucleic acid sequences, which comprises:

a) a first hollow elongated cylinder closed at one end having a plurality of chambers, each chamber having an upper end and a lower end;

b) a second hollow elongated cylinder positioned contiguously inside said first cylinder and having an upper end and a lower end with an aperture and sealing lip interposed and connecting via rotation said lower end of the second cylinder to said upper end of each chamber of said first cylinder, said second cylinder further having three indexing notches disposed equilaterally on the upper end of the cylinder; and c) a cover integrally hinged to the open end of the first cylinder, said cover having a reaction bead chamber integral with a knife-edge, said chamber housing a reaction bead and hermetically sealed with a membrane, said cover further having an indexing pin disposed diametrically to the hinge for indexing with said notches during rotation of said first cylinder in relation to said second cylinder.

2. The device of claim 1 wherein the second hollow elongated cylinder further comprises extraction means and amplification means.

3. The device of claim 2 wherein the extraction means comprises dry lysing reagent for nucleic acid extraction.

4. The device of claim 2 wherein the amplification means comprises polymerases or ligases.

5. The device of claim 1 wherein said plurality of chambers of said first hollow elongated cylinder comprises a reservoir chamber and a detection chamber.

6. The device of claim 5 wherein said reservoir chamber is defined by the contiguous sides of the first hollow elongated cylinder, said detection chamber, and a porous membrane, said porous membrane having pores of a size to enable waste fluid to pass through.

7. The device of claim 5 wherein said detection chamber further comprises detection means.

8. The device of claim 7 wherein said detection means comprises an absorbent pad and a strip having colored microparticles and capture zones.

9. The device as defmed in claim 1, wherein the nucleic acid sequence to be amplified is any specific nucleic acid sequence.

* * * * *

UNITED STATES PATENT AND TRADEMARK OFFICE

CERTIFICATE OF CORRECTION

PATENT NO. : 5,955,351
DATED : September 21, 1999
INVENTOR(S) : John C. Gerdes et al.

It is certified that error appears in the above-identified patent and that said Letters Patent is hereby corrected as shown below:

Column 1,
Line 4, above "RELATED APPLICATIONS" insert the following paragraph:

-- CONTRACTUAL ORIGIN OF THE INVENTION

This invention was made with United States Government support under cooperative agreement number 70NANB5H1109 awarded by the National Institute of Standards and Technology (NIST). The United States Government has certain rights in the invention. --

Signed and Sealed this

Twenty-ninth Day of June, 2004

JON W. DUDAS
*Acting Director of the United States Patent and Trademark Office*

SEQUENCE LISTING (1) GENERAL INFORMATION:

(iii) NUMBER OF SEQUENCES: 13

(2) INFORMATION FOR SEQ ID NO:1:

(i) SEQUENCE CHARACTERISTICS:

(A) LENGTH: 52 bases
(B) TYPE: nucleic acid
(C) STRANDEDNESS: single
(D) TOPOLOGY: linear (xi) SEQUENCE DESCRIPTION: SEQ ID NO:1:

AATTCTAATA CGACTCACTA TAGGGTGCTA TGTCACTTCC 40

CCTTGGTTCT CT 52

(2) INFORMATION FOR SEQ ID NO:2:

(i) SEQUENCE CHARACTERISTICS:
(A) LENGTH: 29 bases
(B) TYPE: nucleic acid
(C) STRANDEDNESS: single
(D) TOPOLOGY: linear (xi) SEQUENCE DESCRIPTION: SEQ ID NO:2:

AGTGGGGGGA CATCAAGCAG CCATGCAAA 29

(2) INFORMATION FOR SEQ ID NO:3:

(i) SEQUENCE CHARACTERISTICS:
(A) LENGTH: 20 bases
(B) TYPE: nucleic acid
(C) STRANDEDNESS: single
(D) TOPOLOGY: linear (xi) SEQUENCE DESCRIPTION: SEQ ID NO:3:

TGGCCTGGTG CAATAGGCCC 20

(2) INFORMATION FOR SEQ ID NO:4:

(i) SEQUENCE CHARACTERISTICS:
(A) LENGTH: 20 bases
(B) TYPE: nucleic acid
(C) STRANDEDNESS: single
(D) TOPOLOGY: linear (xi) SEQUENCE DESCRIPTION: SEQ ID NO:4:

CCCATTCTGC AGCTTCCTCA 20

(2) INFORMATION FOR SEQ ID NO:5:

(i) SEQUENCE CHARACTERISTICS:
(A) LENGTH: 15 bases
(B) TYPE: nucleic acid
(C) STRANDEDNESS: single
(D) TOPOLOGY: linear (xi) SEQUENCE DESCRIPTION: SEQ ID NO:5:

CGATCGAGCA AGCCA 15

(2) INFORMATION FOR SEQ ID NO:6:

(i) SEQUENCE CHARACTERISTICS:
(A) LENGTH: 15 bases
(B) TYPE: nucleic acid
(C) STRANDEDNESS: single
(D) TOPOLOGY: linear (xi) SEQUENCE DESCRIPTION: SEQ ID NO:6:

CGAGCCGCTC GCTGA 15

(2) INFORMATION FOR SEQ ID NO:7:

(i) SEQUENCE CHARACTERISTICS:

(A) LENGTH: 40 bases
(B) TYPE: nucleic acid
(C) STRANDEDNESS: single
(D) TOPOLOGY: linear (xi) SEQUENCE DESCRIPTION: SEQ ID NO:7:

ACCGCATCGA ATGCATGTCT CGGGTAAGGC GTACTCGACC 40

(2) INFORMATION FOR SEQ ID NO:8:

(i) SEQUENCE CHARACTERISTICS:
(A) LENGTH: 40 bases
(B) TYPE: nucleic acid
(C) STRANDEDNESS: single
(D) TOPOLOGY: linear (xi) SEQUENCE DESCRIPTION: SEQ ID NO:8:

CGATTCCGCT CCAGACTTCT CGGGTGTACT GAGATCCCCT 40

(2) INFORMATION FOR SEQ ID NO:9:

(i) SEQUENCE CHARACTERISTICS:
(A) LENGTH: 91 bases
(B) TYPE: nucleic acid
(C) STRANDEDNESS: single
(D) TOPOLOGY: linear (xi) SEQUENCE DESCRIPTION: SEQ ID NO:9:

TGGACCCGCC AACAAGAAGG CGTACTCGAC CTGAAAGACG 40

TTATCCACCA TACGGATAGG GGATCTCAGT ACACATCGAT 80

CCGGTTCAGC G 91

(2) INFORMATION FOR SEQ ID NO:10:

(i) SEQUENCE CHARACTERISTICS:
(A) LENGTH: 20 bases
(B) TYPE: nucleic acid
(C) STRANDEDNESS: single
(D) TOPOLOGY: linear (xi) SEQUENCE DESCRIPTION: SEQ ID NO:10:

AAAGATGTAG AGGGTACAGA 20

(2) INFORMATION FOR SEQ ID NO:11:

(i) SEQUENCE CHARACTERISTICS:
(A) LENGTH: 24 bases
(B) TYPE: nucleic acid
(C) STRANDEDNESS: single
(D) TOPOLOGY: linear (xi) SEQUENCE DESCRIPTION: SEQ ID NO:11:

AATCTGTACC CTCTACATCT TTAA 24

(2) INFORMATION FOR SEQ ID NO:12:

(i) SEQUENCE CHARACTERISTICS:
(A) LENGTH: 28 bases
(B) TYPE: nucleic acid
(C) STRANDEDNESS: single
(D) TOPOLOGY: linear (xi) SEQUENCE DESCRIPTION: SEQ ID NO:12:

ATAATCCACC TATCCCAGTA GGAGAAAT 28

(2) INFORMATION FOR SEQ ID NO:13:

-continued

```
    (i) SEQUENCE CHARACTERISTICS:
         (A) LENGTH:   28 bases
         (B) TYPE:     nucleic acid
         (C) STRANDEDNESS:  single
         (D) TOPOLOGY: linear

   (xi) SEQUENCE DESCRIPTION:    SEQ ID NO:13:

TTTGGTCCTT GTCTTATGTC CAGAATGC                                       28
```